United States Patent [19]

Boie et al.

[11] 4,049,458
[45] Sept. 20, 1977

[54] PHOTOGRAPHIC SILVER HALIDE MATERIAL CONTAINING 2-EQUIVALENT YELLOW COUPLERS

[75] Inventors: Immo Boie, Cologne; Dieter Lowski, Bergheim Erft, both of Germany

[73] Assignee: AGFA-Gevaert, A.G., Germany

[21] Appl. No.: 604,311

[22] Filed: Aug. 13, 1975

Related U.S. Application Data

[63] Continuation-in-part of Ser. No. 476,388, June 5, 1974.

[51] Int. Cl.$^2$ .................................................. G03C 1/40
[52] U.S. Cl. .................................. 96/100 N; 96/56.5; 260/562 R
[58] Field of Search .............................. 96/100, 56.5; 260/562 R

[56] References Cited

U.S. PATENT DOCUMENTS

| | | | |
|---|---|---|---|
| 3,617,291 | 11/1971 | Sawdey | 96/100 |
| 3,770,436 | 11/1973 | Fujiwhara et al. | 96/100 |
| 3,808,945 | 5/1974 | Matsuo et al. | 96/100 |

*Primary Examiner*—J. Travis Brown
*Attorney, Agent, or Firm*—Connolly and Hutz

[57] ABSTRACT

Desirable 2-equivalent yellow couplers carry at the coupling position a monocyclic pyrrole, diazole or triazole ring attached to the coupling position of the yellow coupler by a nitrogen atom, which ring can be split off in the coupling reaction.

Photographic 2-equivalent yellow couplers with nitrogen-containing heterocyclic splittable groups having such nitrogen bonded to the coupling position of the couplers, are prepared by reacting a corresponding 2-equivalent yellow coupler containing a halogen such as chlorine in the coupling position with the nitrogen-containing heterocyclic compound that supplies the splittable group, in the presence of base and in the further presence of hexamethylphosphoric acid triamide as solvent.

4 Claims, No Drawings

PHOTOGRAPHIC SILVER HALIDE MATERIAL CONTAINING 2-EQUIVALENT YELLOW COUPLERS

This application is a continuation-in-part of application Ser. No. 476,388 filed June 5, 1974.

The present invention relates to new 2-equivalent yellow couplers suitable for color photographic materials, and to a process for producing such couplers.

It is known to produce yellow photographic images by developing the exposed silver halide in a light-sensitive silver halide emulsion layer with a color developer in the presence of a color coupler. Simple couplers for producing a yellow image contain an active methylene group which reacts with the oxidized color developer during the process of color development. This reaction requires four equivalents of developable silver halide to produce one mol of yellow dye and these couplers are therefore known as 4-equivalent couplers. Other couplers are known which contain a methylene group in which one hydrogen has been substituted by a group which can be split off during the coupling reaction. In this case only two equivalents of developable silver halide are required to form the dye. These couplers are therefore known as 2-equivalent couplers.

Inasmuch as the quantity of silver halide required to form a given quantity of dye with a 2-equivalent coupler is about half the quantity required in the case of a 4-equivalent coupler, a smaller quantity of silver halide may be used for preparing the light-sensitive recording material. A thinner emulsion layer may therefore be used, and this in turn has an advantageous effect on resolution capacity of the photographic material and sharpness of the image.

Among the 2-equivalent yellow couplers known in the art, those which contain chlorine as splittable substituent have proved in practice to be sufficiently rapid to enable satisfactory color densities even when very short processing methods are employed. However 2-equivalent yellow couplers which contain splittable chlorine frequently have a deleterious effect on the photographic properties of the silver halide emulsion. As described in British patent specification No. 1,351,395, only certain yellow couplers based on benzoylacetanilide and containing splittable chlorine are photographically sufficiently inert to cause an acceptable low level of fogging during development. However they are generally not satisfactory with respect to the photographic requirement that unprocessed photographic material containing the coupler withstand storage under moist, warm conditions without significantly increased fogging.

It is one of the objects of the present invention to provide new 2-equivalent yellow couplers which are easily prepared and the reactivity of which in color photographic development processes are sufficiently high, at least comparable to that of 2-equivalent yellow couplers containing splittable chlorine, and which do not deleteriously affect the photographic properties of the color photographic materials.

It has now been found that improved yellow 2-equivalent couplers have an activated open-chain ketomethylene structure in which one hydrogen of the methylene group is substituted by a nitrogen of a monocyclic aromatic pyrrole, diazole or triazole group that is photographically relatively inert except that it splits off during chromogenic development.

The couplers of the present invention can be represented by the following general formula:

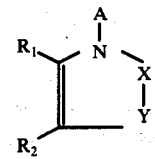

wherein

A represents a yellow coupler structure substituted on the methylene group, e.g. an open-chain ketomethylene coupler group such as in an acylacetonitrile or acylacetyl coupler;

X and Y represent the ring members required to complete an aromatic pyrrole, diazole or triazole ring which is monocyclic, such as pyrrole, imidazole, pyrazole or 1,2,3-triazole, which ring members may themselves be substituted by any substitutents for splittable groups on yellow couplers, and which may be alike or different, e.g. by alkyl such as methyl, isopropyl or in particular trifluoroalkyl such as trifluormethyl or preferably by electronegative substituents, such as halogen, nitro, cyano, sulfo, carboxy, carbalkoxy (a better name for which is alkoxycarbonyl);

$R_1$ and $R_2$ which may be the same or different, represent the presence or absence of substituents commonly found in splittable groups of yellow couplers, e.g. hydrogen, alkyl, alkoxy, alkylthio, aryl, acylamino, such as carbamyl and sulfamyl, sulfonamido, acyloxy, acyl, e.g. alkoxycarbonyl (carbalkoxy), carboxy, nitro, halogen or cyano.

The 2-equivalent coupler structure of the present invention is derived from conventional 4-equivalent couplers which form a yellow dye. Those structures are well known and described e.g. in U.S. Pat. Nos. 3,447,923 and 3,617,799. Preferred couplers accordingly are those of the above general formula in which A represents an open-chain ketomethylene yellow coupler structure, e.g. acylacetonitrile or acylacetyl, in particular of the following formula I:

wherein

B represents an alkyl group preferably containing from 1 to 32 carbon atoms, more preferably 1 to 18 carbon atoms, which may be branched or straight chained, and, in the case of a secondary or tertiary alkyl group, the secondary or tertiary carbon atom is preferably directly attached to the carbonyl group; an alkoxyalkyl group; a bicycloalkyl group; a heterocyclic group; or an aryl group which may be substituted by alkyl preferably containing 1 to 18 carbon atoms, or by halogen, e.g. fluorine or bromine, acetamido, carbamyl, sulfamyl, sulfonamido or carboxy; and B' represents a cyano group or the group

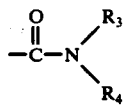

R₃ represents hydrogen or an alkyl group preferably containing 1 to 5 carbon atoms, for example a methyl or ethyl group; and R₄ represents an alkyl group, preferably containing 1 to 18 carbon atoms; or preferably an aryl group, for example a phenyl group which may be substituted with an alkyl group containing 1 to 18 carbon atoms, an alkoxy group containing 1 to 18 carbon atoms, halogen, e.g. fluorine or bromine, acylamino, carbamyl, sulfamyl, sulfonamido or carboxy.

The new yellow couplers according to the invention have a high coupling capacity, i.e. they produce dye images with a high color density, and they are eminently suitable for use in light-sensitive silver halide emulsion layers of color photographic single or multilayered materials.

The yellow couplers need not necessarily be incorporated in the light-sensitive layers but may be accommodated in a layer of binder adjacent to the light-sensitive silver halide emulsion layer.

Depending on the choice of substituents R₃, R₄, B or B' according to the definitions given above, the yellow couplers according to the invention may be used either as diffusion-fast couplers or as non-diffusion-fast couplers to form yellow color images in photographic materials. To obtain sufficiently high diffusion-fastness, the substituents R₃, R₄ or B, preferably B or B', are provided with groups which confer diffusion-fastness, e.g. straight or branched chain alkyl groups containing 10 to 18 carbon atoms, or they may be substituted with alkyl substituted phenoxy groups which may be attached to the groups B,B',R₃ or R₄ which may themselves be aromatic, either directly or indirectly, for example through —O—, —S—, —CONH—, —NHCO—, —SO₂NH— or other intermediate links.

If the couplers are required to be soluble in alkali, at least one of the groups B,B',R₃ or R₄ may carry groups which confer solubility in alkali, preferably sulfo groups.

Couplers according to the present invention which are not diffusion-resistant are particularly suitable for use in developer solutions for developing the yellow dye image in exposed photographic color films which do not contain yellow coupler.

Particularly preferred 2-equivalent yellow couplers according to the present invention contain, as their splittable group, an aromatic imidazole ring containing in particular short chain alkyl substituents with 1 to 4 carbon atoms preferably methyl, or electro-negative substituents such as nitro, chloro, carboxy, cyano or especially an alkoxy-carbonyl group in which the alkoxy contains 1 to 4 carbon atoms.

The following are examples of suitable yellow couplers according to the present invention:

1) 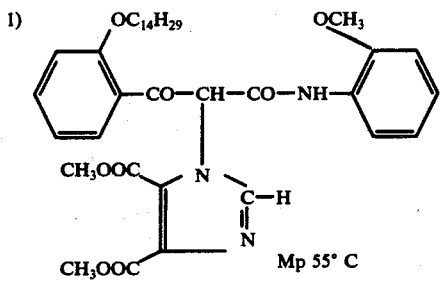
Mp 55° C

2) 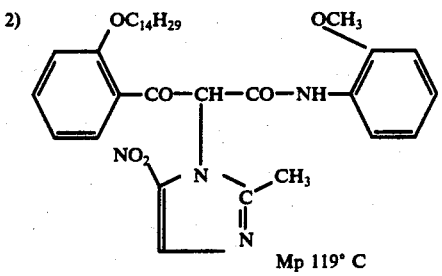
Mp 119° C

3) 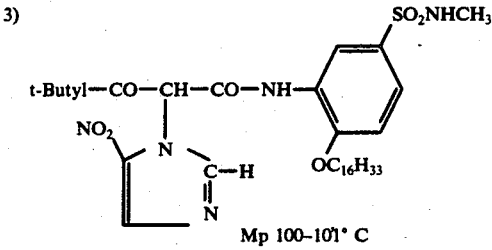
Mp 100-101° C

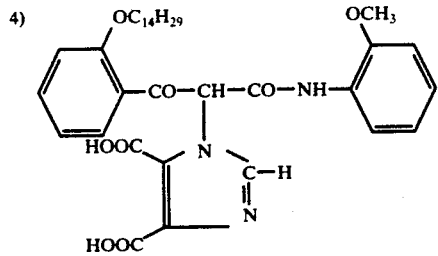
4)
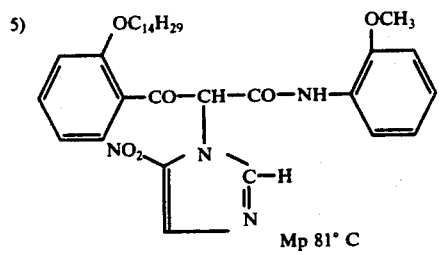
5) Mp 81° C
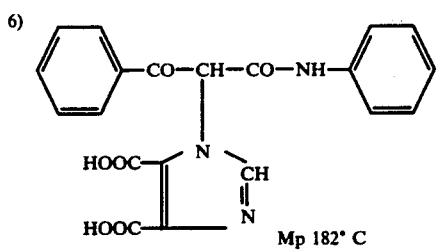
6) Mp 182° C
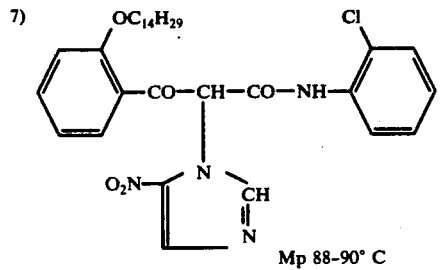
7) Mp 88-90° C
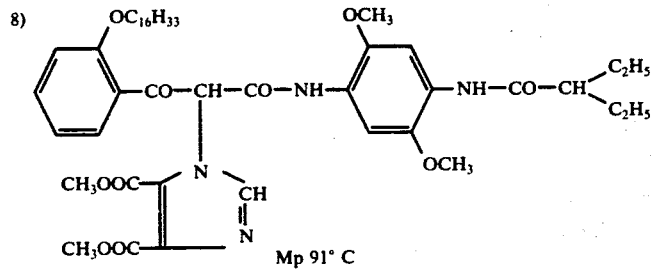
8) Mp 91° C -continued
9) 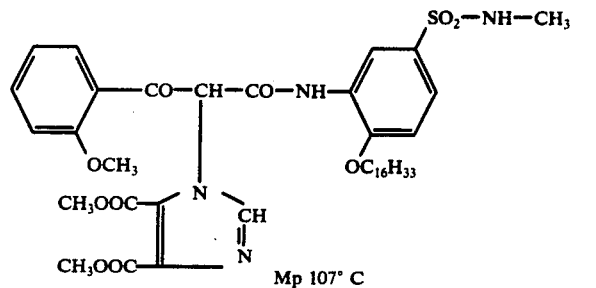
Mp 107° C
10) 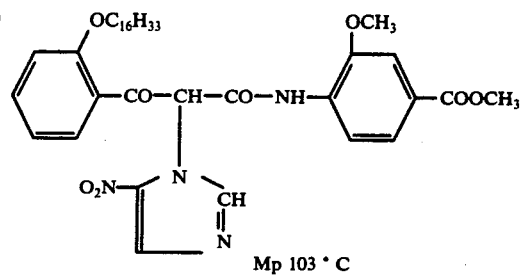
Mp 103° C
11) 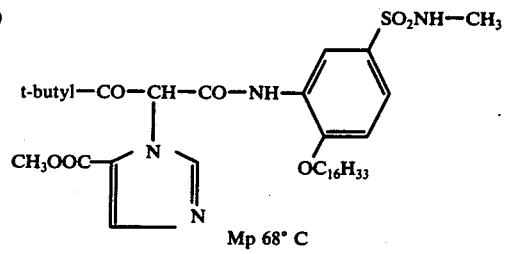
Mp 68° C
12) 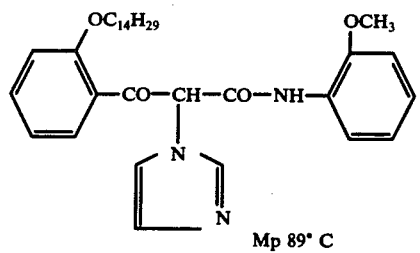
Mp 89° C
13) 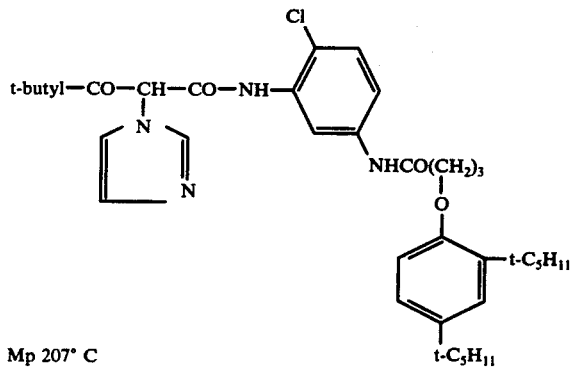
Mp 207° C
14) 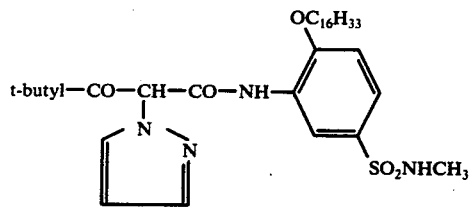
Mp 100° C 15) 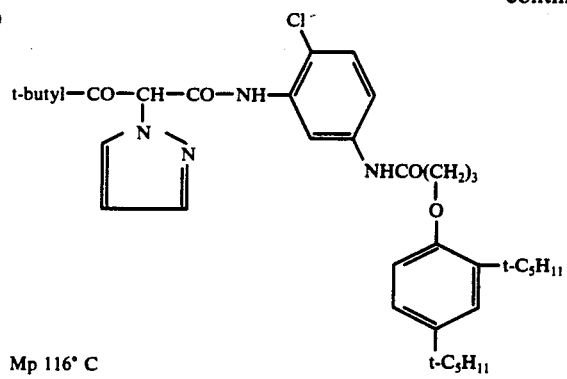
Mp 116° C
16) 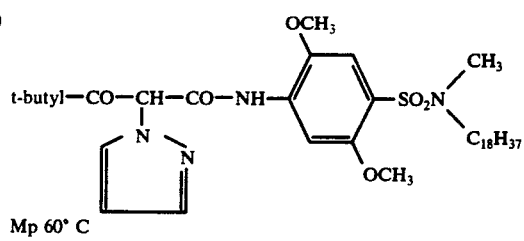
Mp 60° C
17) 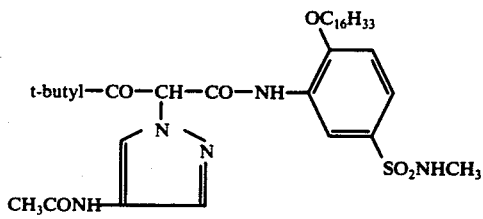
Mp 93° C
18) 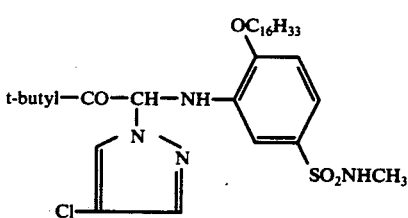
Mp 78° C
19) 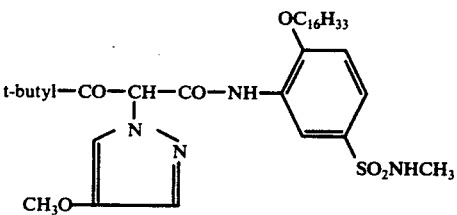
Mp oily
20) 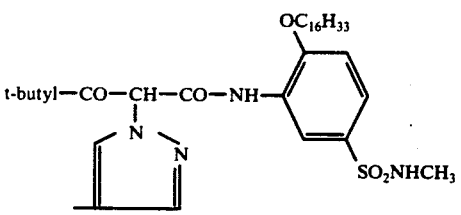
oily -continued
21) 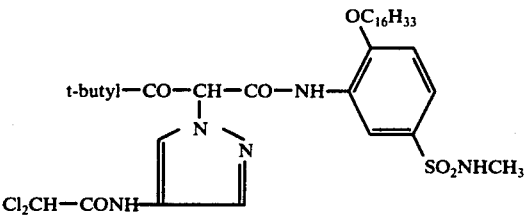
Mp 123–124° C
22) 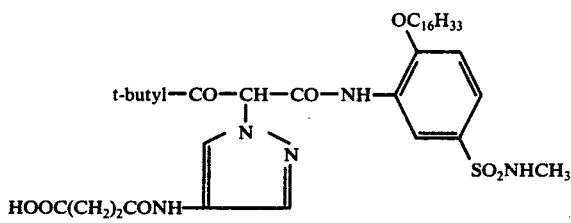
Mp 105–108° C
23) 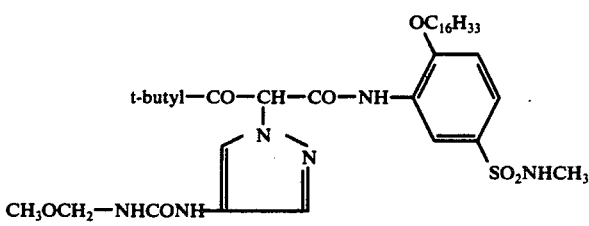
Mp oily
24) 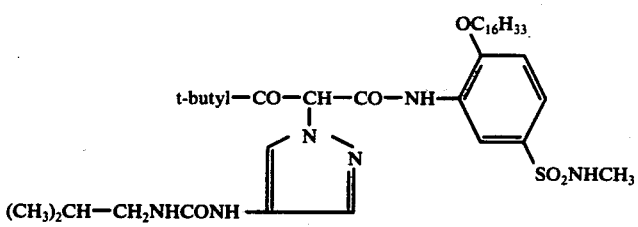
Mp 85–92° C
25) 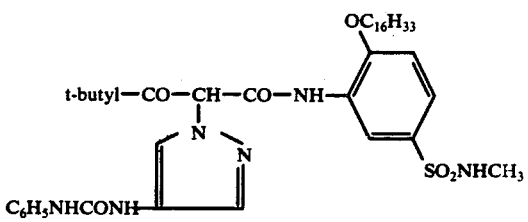
Mp 141° C
26) 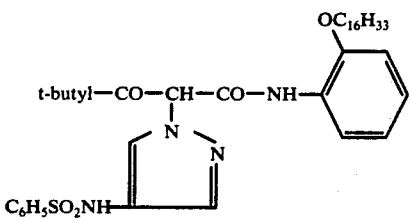
Mp 61° C -continued
27) 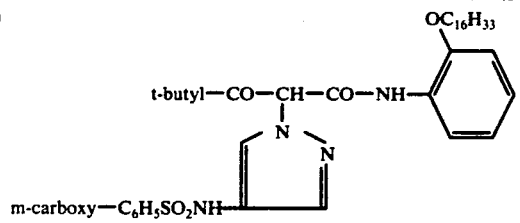
Mp 149° C
28) 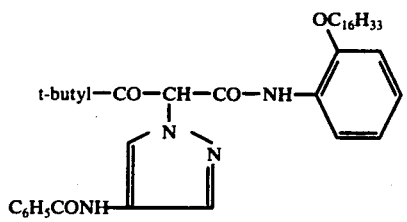
Mp 73° C
29) 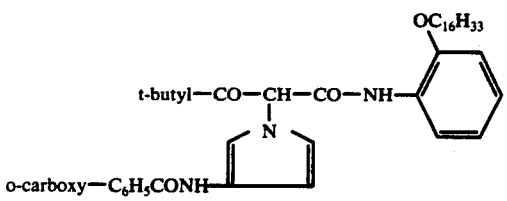
Mp 165° C
30) 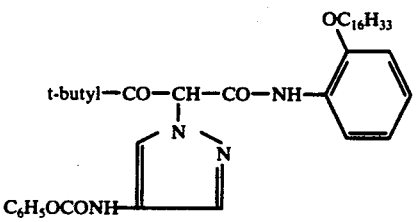
Mp 70–73° C
31) 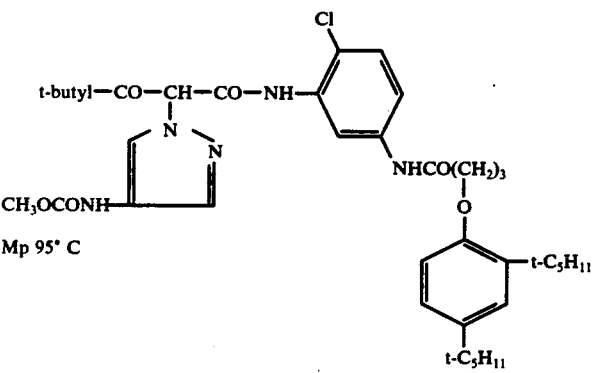
Mp 95° C
32) 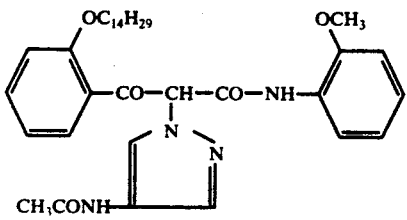
Mp 103–111° C -continued
33) 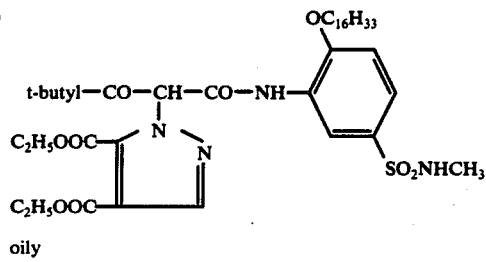
oily
34) 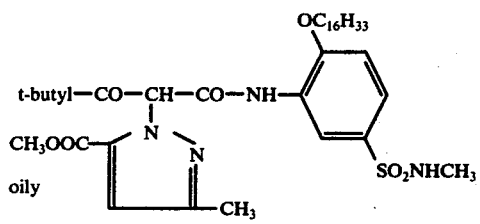
oily
35) 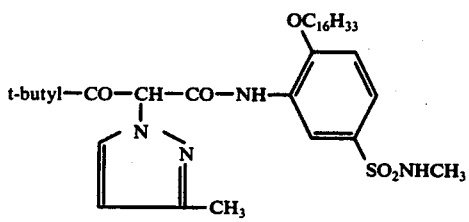
oily
36) 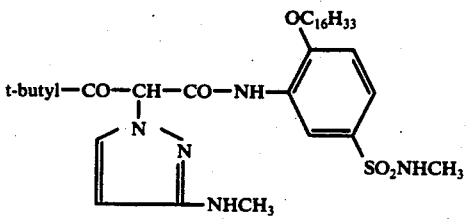
Mp 63-70° C
37) 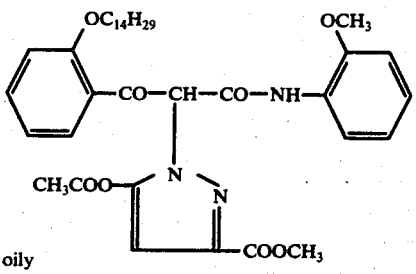
oily 38) 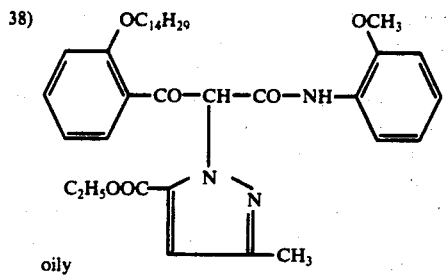
oily 39) 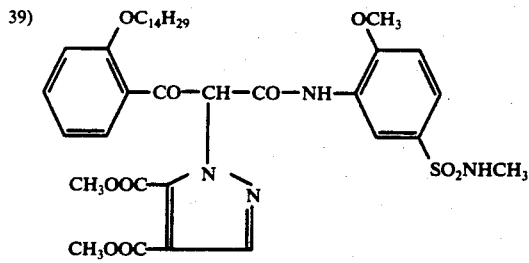
Mp 75–81° C 40) 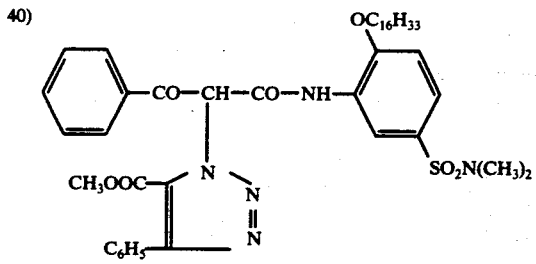
Mp 80–82° C 41) 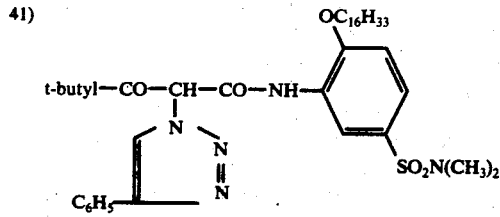
Mp 78° C 42) 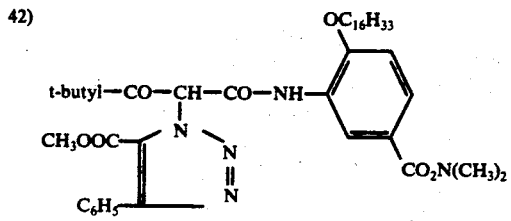
Mp 88° C Those yellow couplers according to the invention which are diffusion resistant are highly emulsifiable, have excellent resistance to crystallization in the casting solution and in the photographic material, and do not impair the photographic properties of the emulsions even under extreme conditions of storage.

The couplers of the invention are very suitable as 2-equivalent yellow couplers. They are capable of producing yellow images with a high image density by requiring less developable silver halide if compared to the image density produced by a 4-equivalent yellow coupler.

The yellow couplers of the invention are unexpectedly even superior to yellow couplers having as splittable group monocyclic nonaromatic nitrogen-containing 5-membered rings having two carbonyl groups adjacent to that nitrogen atom which is attached to the carbon atom in the coupling position of the said yellow couplers, such as couplers containing an imidazolidindione-(2,5) splittable group or an oxazolinedione-(2,4)splittable group.

Compared to the first of these couplers (disclosed in German Offenlegungsschrift No. 2,213,461) the couplers of the invention are easily emulsifiable and have a lesser tendency to crystallize out of photographic layers.

Compared to both of said couplers the inventive couplers are much more stable in photographic layers, so that even when they are stored under moist warm conditions, in an exposed photographic material prior before the processing thereof, the photographic properties of the layer and in particular fogging are only immaterially affected, whereas with said prior art couplers either a loss in density (due to crystallization of the coupler in the layer) or an increase of the fogging materially affects the quality of the photographic image obtained.

The yellow couplers according to the invention can easily be prepared by reacting the corresponding 2-equivalent couplers A—Cl wherein A has the meaning indicated above and Cl is the removable substituent, with a compound of formula II

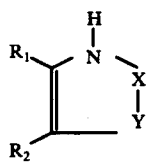

wherein

X, Y, $R_1$ and $R_2$ have the meanings specified above, in the presence of a base in the usual manner, e.g. as described in German Offenlegungsschrift No. 2,213,461.

As stated above, the substituents of the heterocyclic groups are those well-known in splittable groups in yellow couplers.

If $R_1$ or $R_2$ represents, or X and Y contains, alkyl, it is preferably an alkyl group having up to 5 carbon atoms such as a methyl, trifluoromethyl or propyl group.

If $R_1$ or $R_2$ represents, or X and Y contains, an acyl group the acyl group, is preferably derived from carbonic acid derivatives such a monoesters of carbonic acid with alcohols having up to 5 carbons, or from aliphatic or aromatic carboxylic acids or sulfonic acids such as benzoyl groups and short-chained alkoxycarbonyl groups (e.g. ethoxycarbonyl, methoxycarbonyl) or short-chained alkanoyloxy groups (e.g. acetoxy).

$R_1$ or $R_2$ may also represent, or X and Y may contain, sulfonamido groups (e.g. alkylsulfonylamine), carbonamido groups (e.g. methoxycarbonylamino, acetamido, benzoylamino), and carbamyl or sulfamyl one or two hydrogen atoms of which may be substituted by short-chained alkyl, aryl such as phenyl, or aralkyl groups, such as benzyl or phenethyl groups.

The preparation reaction may be carried out in an aprotic solvent, e.g. acetonitrile or dimethylformamide, using as base either an aliphatic amine, e.g. triethylamine, or a basic heterocyclic compound such as pyridine, or an alkali metal alcoholate such as sodium alcoholate. This generally produces the yellow couplers of the present invention more easily and in higher yields than the couplers described in German Offenlegungsschrift No. 2,213,461. For example the o-alkoxy substituted benzoyl acetanilide couplers of that Offenlegungsschrift can only be obtained by boiling the reactants for days in acetonitrile and even then in only moderate yields.

Furthermore, it has been found according to the present invention that when 2-equivalent couplers of the formula A—Cl or A—Br, that is having chlorine or bromine as splittable moiety are reacted with the compound of formula II wherein X, Y, $R_1$ and $R_2$ have the meanings specified above, and with a base, at temperatures of 20° to 100° C, preferably 40° to 80° C, in the presence of hexamethylphosphoric acid triamide as solvent, 2-equivalent couplers are obtained in excellent yields and with a high degree of purity.

In this improved reaction according to the invention, the 2-equivalent coupler which contains chlorine as splittable moiety and the heterocyclic compound of formula II may generally be used in equimolar quantities although it is preferred to use a 1 to 200% molar excess of compound of formula II, based on the quantity of 2-equivalent coupler used.

It is generally sufficient to add the base in equimolar quantities, based on the compound of formula II. If desired, however, the base may also be used in a 1 to 200% molar excess.

The base used in the reaction according to the invention may be any of the basic compounds commonly used in the art, e.g. those defined above, although sodium methylate is preferred.

If desired, however, part of the hexamethylphosphoric acid triamide used as solvent, preferably not more than 50%, may be replaced by conventional polar sol,ents such as dioxane, ethers, alcohols, acetonitrile or dimethylformamide.

The quantity of hexamethyl phosphoric acid triamide used as solvent is not critical. It depends on the solubility of the reactants in the solution and can be determined by a few laboratory tests. Quantities of 5 to 100 ml of hexamethyl phosphoric acid triamide per 1 g of coupler compound have generally been found to be sufficient.

The yellow couplers according to the invention can be precipitated from the reaction mixtures in the usual manner by mixing them with a mixture of ice, water and hydrogen chloride, separated, washed, and purified by dissolving the washed and dried reaction product in a solvent which is immiscible with water, e.g. chloroform or, preferably, in hot ether, and colorless crystals of the yellow couplers according to the invention can be obtained with an excellent degree of purity by adding petroleum ether and cooling the solvent mixture, so that no further purification processes such as recrystallization are generally required.

The preparation of coupler No. 5 according to the invention is described in detail below:

15 g of α-chloro-α-(2-tetradecyloxy)-benzoyl-2-methoxyacetanilide are dissolved in 100 ml of hexamethylphosphoric acid triamide, and 7 g of 4-nitroimidazole and 12 ml of 4 molar sodium methylate solution are added. After 3 hours' stirring at 40° C, the reaction mixture is poured on a mixture of ice and hydrogen chloride.

The reaction mixture is then filtered off, washed with water, dried on clay and dissolved in hot ether. After the removal of minor impurities by filtration, about 10 ml of petroleum ether are added to the hot filtrate which is then cooled. After suction filtration and washing with petroleum ether, 9.5 g of colorless crystals of coupler 5 are obtained. M.p. 81° C.

The other couplers of the present invention may be prepared in a similar manner. Indeed this process also may readily and inexpensively produce any kind of 2-equivalent yellow coupler having in the coupling position an organic group which is attached by a nitrogen atom to the carbon atom of the coupling position.

Thus prior art couplers of this type are very easily prepared by this technique.

When preparing the light-sensitive color material according to the invention, the diffusion-resistant yellow couplers according to the above general formula may be incorporated by any known technique in the casting composition of the silver halide emulsion layers or of other colloid layers which are in waterpermeable relation thereto. For example, the water-soluble color couplers, i.e. those which contain one or more water-solubilizing groups such as a sulfo or carboxyl group (in acid or salt form) may be incorporated in the casting composition of the layer in question by applying them from an aqueous solution, while those color couplers which are insoluble or insufficiently soluble in water may be applied from a solution of suitable water-miscible or immiscible high boiling or low boiling organic solvents or mixtures thereof. The resulting solution is then dispersed in a hydrophilic colloid composition, optionally in the presence of a wetting or dispersing agent, this colloid composition constituting either all or only part of the binder of the final colloid layer. The hydrophilic colloid composition may, of course, contain any other ingredients in addition to the colloid. The waterinsoluble color couplers which contain fluorosulfonyl groups or carboxylic acid ester groups such as ethoxycarbonyl groups may also be converted by alkaline hydrolysis into the corresponding sulfonic acids or carboxylic acids which can be incorporated in the hydrophilic colloid compositions by applying them in the form of aqueous solutions of their alkali metal salts.

The solution of color couplers need not be directly dispersed or dissolved in the casting composition of the silver halide emulsion or some other water permeable layer. The solution may advantageously first be dispersed or dissolved in an aqueous light-insensitive solution of a hydrophilic colloid, whereupon the resulting mixture, optionally after removal of the organic solvent used, is intimately mixed with the casting composition of the light-sensitive silver halide emulsion layer or other water permeable layer just before casting. Further details about particularly suitable techniques for incorporating color couplers in hydrophilic colloid layers of a photographic material may be found in published Dutch patent application Nos. 6,516,432; 6,516,424; 6,600,098; 6,600,099 and 6,600,628; Belgian patent 750,889; U.S. Pat. No. 2,304,940 and British patent specification No. 791,219.

To prepare photographic color images according to the invention, an exposed silver halide emulsion layer is developed with an aromatic primary amino developer substance in the presence of a color coupler according to the invention. The developer substances used may be any color developer substances which are capable of yielding azomethine dyes. Suitable developer substances include aromatic compounds such as p-phenylenediamine and its derivatives, for example, N,N-dialkyl-p-phenylenediamines such as N,N-dialkyl-N'-sulfomethyl-p-phenylenediamines and N,N-dialkyl-N'-carboxymethyl-p-phenylenediamine.

The emulsions may also be sensitized with polyalkylene oxide derivatives, e.g. with a polyethylene oxide which has a molecular weight of between 1000 and 20,000, or with condensation products of alkylene oxide and aliphatic alcohols, glycols, cyclic dehydration products of hexitols, with alkyl-substituted phenols, aliphatic carboxylic acids, aliphatic amines, aliphatic diamines and amides. The condensation products have a molecular weight of at least 700, preferably more than 1000. These sensitizers may, of course, be combined in order to achieve special effects, as described in Belgian Patent No. 537,278 and British patent specification No. 727,982.

The emulsions must have sufficient sensitivity in the blue spectral region. Non-sensitized emulsions whose sensitivity is due to the intrinsic sensitivity of the silver halides are generally used for this purpose although the silver halide emulsions may be spectrally sensitized in the blue region, e.g. by means of sensitizers of the kind described in British patent specification No. 1,285,078.

The emulsions may contain the usual stabilizers, e.g. homopolar or salt-type compounds of mercury which contain aromatic or heterocyclic rings such as mercaptotriazoles, simple mercury salts, sulfonium mercury double salts and other mercury compounds. Azaindenes are also suitable stabilizers, particularly tetra- or penta-azaindenes and especially those which are substituted with hydroxy or amino groups. Compounds of this kind have been described in the article by BIRR, Z. Wiss. Phot. 47 (1952) 2-58.

Suitable light-sensitive emulsions are emulsions of silver halides such as silver chloride, silver bromide or mixtures thereof, which may have a small silver iodide content of up to 10 mols-%, used in one of the conventional hydrophilic binders. The binder used for the photographic layers is preferably gelatin, although this may be partly or completely replaced by other natural or synthetic binders. Suitable natural binders are e.g. alginic acid and its derivatives such as salts, esters or amides, cellulose derivatives such as carboxymethylcellulose, alkylcellulose such as hydroxyethylcellulose, starch or its derivatives such as ethers or esters, or carrageenates. The synthetic binders include polyvinyl alcohol; partly saponified polyvinyl acetate and polyvinyl-pyrrolidone.

The emulsions may also be chemically sensitized, e.g. by adding sulfur compounds such as allylisothiocyanate, allylthiourea and sodium thiosulfate at the state of chemical ripening. Reducing agents may also be used as chemical sensitizers, e.g. the tin compound described in Belgian patent Nos. 493,464 and 568,687, or polyamines such as diethylene triamine or aminoethane sulfinic acid derivatives, e.g. according to Belgian patent No. 547,323.

Noble metals such as gold, platinum, palladium, iridium, ruthenium or rhodium and compounds of these metals are also suitable chemical sensitizers. This method of chemical sensitization has been described in the article by R. KOSLOWSKY, Z. Wiss. Phot. 46 (1951) 65-72.

Other suitable stabilizers include heterocyclic mercapto compounds, e.g. phenylmercaptotetrazole, quaternary benzothiazole derivatives and benzothiazole.

The emulsions may be hardened in the usual manner, for example with formaldehyde or halogenated aldehyde which contains a carboxyl groups, such as mucobromic acid, diketones, methanesulfonic acid esters and dialdehydes.

The advantgeous properties of the couplers according to the invention will be shown below with the aid of some examples.

EXAMPLE 1

2 mmol of Coupler 1 were dissolved in 3 ml of ethyl acetate and then emulsified in 20 ml of a 5 % gelatin solution at 60° C in known manner after the addition of 1 g of dibutylphthalate and 0.16 g of sodium dodecylbenzene sulfonate. The resulting emulsion was then mixed with 85 g of a 7.5 % gelatin solution in which 1.93 g of silver bromide were dispersed and the mixture was diluted with water until the viscosity is sufficiently reduced for casting.

The casting emulsion was cast on a transparent support layer of cellulose triacetate, the coated material prepared in this way was cut into several samples and exposed behind a grey step wedge.

The samples were then developed for one, three or five minutes in a conventional color developer which contains N,N-diethyl-p-phenylenediamine as developer substance, and bleached and fixed in the usual manner.

Color wedges were prepared in a similar manner except that instead of 2 mmol of Coupler 1, 2 mmol of a compound of the following formula:

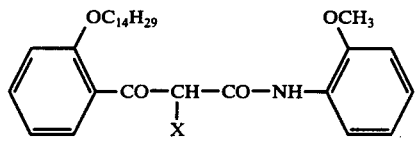

in which X has the meaning specified in Table 1 below were used.

The yellow densities of the individual samples were determined sensitometrically in the usual manner and the results obtained are shown in Table 1.

Table 1

| Coupler | X | $D_{max}$ 1 Min. | 3 Min. | 5 Min. |
|---|---|---|---|---|
| 1 | CH₃OOC—C(N)=CH / CH₃OOC—C=N (imidazole) | 0.70 | 1.71 | 1.98 |
| 5 | NO₂—(N)=CH / =N (imidazole) | 0.532 | 1.4 | 2.02 |
| according to British 1,351,395 | H | 0.126 | 0.308 | 0.574 |
| Coupler 9 of British 1,351,395 | Cl | 0.516 | 1.72 | 1.96 |

As can be seen from Table 1, the reaction velocity of Couplers 1 and 5 according to the invention is comparable to that of comparison coupler 9 from British patent specification No. 1,351,395 since the density values obtained with the various development times are approximately the same.

As can also be seen from Table 1, the 4-equivalent coupler according to British patent specification No. 1,351,395 is clearly inferior to the yellow couplers according to the invention.

EXAMPLE 2

Emulsions were prepared as described in Example 1 using, in each case, 2 mmol of the couplers shown in Table 2 below, and the emulsions were cast as described in Example 1.

The photographic materials obtained in which way were then divided into two portions, Sample A being developed for 5 minutes and processed as described in Example 1 and Sample B being stored in a heating cupboard for 7 days at 57° C and 34% relative humidity before being processed.

The Samples A and B are compared in Table 2 below, the critria used for assessing them being the increase in basic fog values (ΔS) in relative values and the color density loss of Sample B compared with Sample A.

Table 2

| Coupler | X | ΔS | Color density loss |
|---|---|---|---|
|  | H | 0 | 0 |
|  | Cl | +0.33 | 0 |
| 1 | CH₃OOC—C(N)=CH / CH₃OOC—C=N | +0.09 | 0 |
| 4 | HOOC—(N)=CH / HOOC—=N | +0.01 | 0 |
| 5 | NO₂—(N)=CH / =N | +0.01 | 0 |

Table 2 shows that the heating cupboard stability of Couplers 1, 4 and 5 according to the invention is clearly superior to that of Coupler 9 of British Patent No. 1,351,395. The couplers according to the invention are distinguished by their excellent stability so that even when they are stored under moist warm conditions the photographic properties of the layer and in particular fogging are only immaterially affected.

Obviously many modifications and variations of the present invention are possible in the light of the above teachings. It is, therefore, to be understood that within the scope of the appended claims the invention may be practiced otherwise than as specifically described.

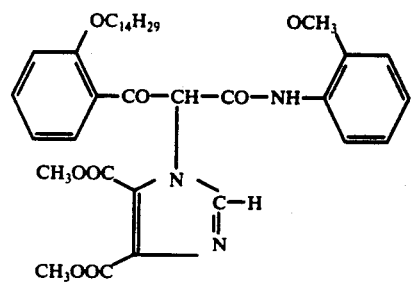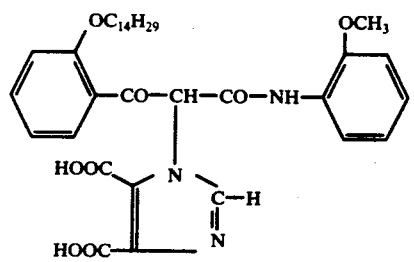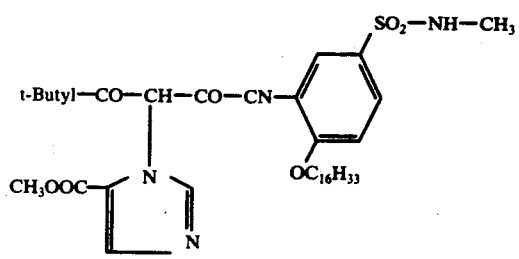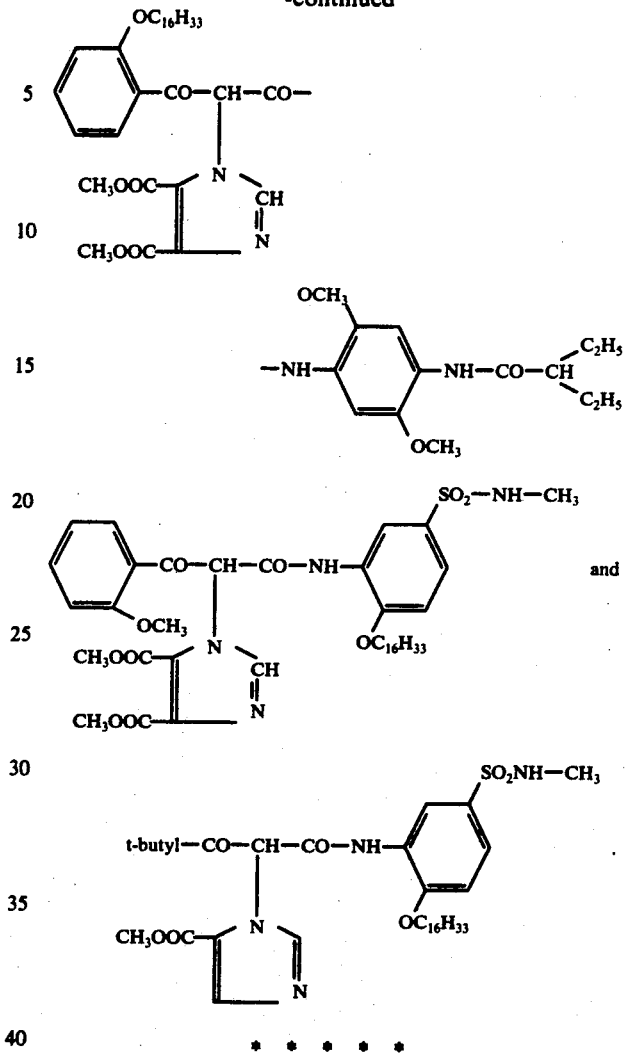

What is claimed:

1. In a light sensitive color photographic material containing at least one silver halide emulsion layer and a 2-equivalent yellow coupler having an activated open-chain ketomethylene coupler structure in which one hydrogen of the methylene group is substituted by a nitrogen of a heterocyclic group which group is photographically relatively inert except that it is split off during chromogenic development, the improvement according to which the splittable group is a monocyclic pyrrole, 1,2-diazole, 1,3-diazole or 1,2,3-triazole group attached to the coupling position of the yellow coupler.

2. The combination of claim 1 wherein the diazole group is an imidazole group.

3. The combination of claim 2 wherein the imidazole group is methoxycarbonyl substituted.

4. The combination of claim 1 in which the yellow coupler is selected from the class consisting of